United States Patent [19]
Bottaccio et al.

[11] 3,976,677
[45] Aug. 24, 1976

[54] PROCESS FOR CARBOXYLATING ORGANIC SUBSTRATES WITH CARBON DIOXIDE IN HYDROCARBON SOLVENTS

[75] Inventors: Giorgio Bottaccio; Gian Paolo Chiusoli; Marcello Marchi, all of Novara, Italy

[73] Assignee: Montedison S.p.A., Milan, Italy

[22] Filed: Apr. 2, 1975

[21] Appl. No.: 564,335

[30] Foreign Application Priority Data
Apr. 3, 1974 Italy .................................. 50019/74

[52] U.S. Cl. ....................... 260/465 D; 260/475 SC; 260/514 R; 260/514 K; 260/515 P; 260/515 R; 260/526 R; 260/537 R
[51] Int. Cl.² ................... C07C 65/18; C07C 121/66
[58] Field of Search ...... 260/465 D, 475 SC, 514 K, 260/514 R, 515 R, 515 P, 533 R, 526 R, 537 R

[56] References Cited
UNITED STATES PATENTS
3,595,907  7/1971  Patmore et al. .................... 260/515

*Primary Examiner*—Lewis Gotts
*Assistant Examiner*—Dolph H. Torrence

[57] ABSTRACT

Carboxylable substrates i.e., ketones, esters, nitroparaffins and nitriles, containing activated hydrogen atoms are carboxylated by reaction with alkaline phenates and $CO_2$ in at least one hydrocarbon solvent selected from aliphatic, alicyclic, aromatic and alkylaromatic hydrocarbon solvents.

8 Claims, No Drawings

PROCESS FOR CARBOXYLATING ORGANIC SUBSTRATES WITH CARBON DIOXIDE IN HYDROCARBON SOLVENTS

THE PRIOR ART

It is known to carboxylate organic substrates containing activated hydrogen atoms with $CO_2$ and with the use of alkaline phenates in a dipolar aprotic medium such as dimethyl-formamide, dimethyl-sulphoxide, etc.

However, the process has the disadvantage of requiring the recovery of the dipolar aprotic solvent by technologically complicated operations. In addition, the use of a dipolar aprotic solvent involves considerable expense, so that the process is uneconomical.

THE PRESENT INVENTION

An object of this invention is to provide a simple, economical process for the carboxylation of organic substrates containing activated hydrogen atoms which does not present the disadvantages of the prior art processes.

That and other objects which will appear hereinafter are accomplished by this invention in accordance with which the carboxylable substrates containing activated hydrogen atoms are carboxylated by reaction with $CO_2$ in the presence of particular alkaline phenates and in at least one solvent selected from aliphatic, alicyclic, aromatic and alkyl-aromatic hydrocarbon solvents.

Suitable alkaline phenates (Li, Na, K, etc.) for use in this process are those substituted by:
a. an alkyl group containing from 3 to 20 carbon atoms and bound to the phenolic nucleus in ortho, meta, para positions through a tertiary or quaternary carbon atom;
b. an alkyl group containing from 1 to 20 carbon atoms and bound to the phenolic nucleus in ortho or meta position through a primary or secondary carbon atom or by a phenyl radical; or
c. at least two alkyl groups containing from 1 to 20 carbon or phenyl groups in ortho and para positions.

The aliphatic, alicyclic, aromatic or alkyl-aromatic hydrocarbon solvents used in the practice of the invention are preferably those having boiling points comprised between 80°C and 250°C, such as, for example, toluene, heptane, 1,2,4-trimethylbenzene, meta-diisopropylbenzene, etc.

Carboxylable substrates are ketones, esters, nitroparaffins or nitriles having the formulae:

$$R_1-CH-COR_3;$$
$$\quad\ \ |$$
$$\quad\ \ R_2$$

$$R_1-CH-CO-CH-R_4$$
$$\quad\ \ |\qquad\qquad\ \ |$$
$$\quad\ \ R_2\qquad\quad\ R_5$$

OR $$A-CH-R_1$$
$$\quad\ \ |$$
$$\quad\ \ R_2$$

in which
$R_1$, $R_2$, $R_4$ and $R_5$, which can be the same or different, represent H or alkyl or aryl radicals;
$R_3$ represents an alkyl, aryl radical or, when $R_1$ is an aryl radical, an o-alkyl or o-aryl radical.
$R_1$ and $R_4$ may be bound to each other by alkyl chains which can be ramified.
A can be a $-NO_2$ group or a dinitroaryl group; when $R_1$ is an aryl radical, A can be the $-CN$ group.

The carboxylated products obtained by the process of this invention have the general formulae:

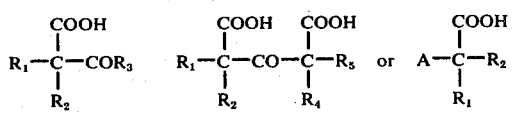

in which the symbols given have the same significance as stated hereinabove.

The phenate (Li, Na, K) salt may be prepared separately or directly in situ starting from phenol and alkaline hydroxide, by azeotropically removing the reaction water by means of the hydrocarbon solvent used for the carboxylating reaction.

The reaction is conducted under substantially conventional parametric conditions. In particular, from 1 to 4 moles of alkaline phenate per 1 mole of organic substrate are preferably used. By employing a ratio between phenate and substrate to be carboxylated of 1:1 and by operating at room temperature, the conversion is lower. However, the selectivity remains high since the substrate is recovered for the most part. Higher conversions are obtained by increasing the 1:1 ratio and/or the temperature.

The reaction can be conducted at a temperature of from room temperature to 100°C, preferably at a temperature of about 50°C.

In practice, in a presently preferred embodiment, the reaction is conducted as follows:

The mixture made up of phenate and solvent, previously saturated with carbon dioxide is added, under stirring and at room temperature to the substrate to be carboxylated, in a ratio ranging from 1 to 4 moles of phenate per 1.0 mole of substrate. The products are isolated and purified by techniques known in general. For instance, the reaction mass is acidified with 10% $H_2SO_4$ and the organic phase is separated and in its turn extracted with a 10% aqueous sodium carbonate solution. The carboxylation product is obtained by acidification, extraction, etc.

The process is particularly advantageous due to the mild operating conditions. An additional advantage is the possibility of employing cheap and readily available solvents.

The products thus obtained prove to be suited for important uses. In particular they may be employed, besides as high-quality intermediates for organic syntheses in general, in the fields of cosmetics, of solvents for cellulose acetate and nitrate, of resins, lacquers, inks, varnishes (benzoyl-acetic acid), of citric acid (beta-keto-glutaric acid), etc.

The following examples are given to illustrate the invention in greater detail and are not intended to be limiting.

EXAMPLE 1

6.7 g of potassium 2,6-di-t-butyl-p-cresolate in 30 cc of toluene were introduced into a 4-neck flask, having a capacity of 100 cc, provided with stirrer, thermometer and gas inlet pipe. In a carbon dioxide atmosphere 3.1 g of acetophenone (phenate: substrate molar ratio = 1 : 1) were added; the whole was stirred at 20°C for 4 hours and then acidified with cold sulphuric acid at 10% concentration. The organic phase separated, and was then extracted with a 10% sodium carbonate aqueous solution. 0.9 g of benzoylacetic acid were isolated by acidification and extraction with ether. 2.3 g of acetophenone were recovered from the organic phase.

EXAMPLE 2

By operating according to the modalities and with the reagents amounts of Example 1, but at a temperature of 50°C, 1.65 g of benzolyacetic acid were isolated.

EXAMPLE 3

By operating with the reagents amounts and according to the modalities of Example 1, but at a temperature of 100°C, 0.95 g of benzoylacetic acid were isolated.

EXAMPLE 4

By operating as illustrated in Example 1, but reducing to 0.85 g the amount of fed acetophenone (molar ratio = 3.6:1), 0.9 g of benzoylacetic acid were obtained.

EXAMPLE 5

By operating according to Example 1, but substituting potassium 2,6-di-t-butyl-p-cresolate with an equivalent amount of sodium salt (6.3 g), 1.0 g of benzoylacetic acid were obtained.

EXAMPLE 6

By operating under the conditions of Example 2, starting from 18 g of potassium 2,6-di-t-butyl-p-cresolate in 80 cc of toluene, and from 1 g of acetone (molar ratio = 4:1), 0.26 g of acetoacetic acid and 1.1 g of beta-keto-glutaric acid were obtained as sodium salts.

EXAMPLE 7

By operating as in Example 1, starting from 4.5 g of potassium 2,6-di-t-butyl-p-cresolate and 1.1 g of nitromethane (molar ratio = 1:1), 0.44 g of nitroacetic acid were obtained.

EXAMPLE 8

By operating as in Example 2, starting from 4.5 g of potassium 2,6-di-t-butyl-p-cresolate and 2.6 g of methyl phenyl-acetate (molar ratio = 1:1), 1.2 g of methyl monoester of phenyl-malonic acid were obtained.

EXAMPLE 9

Starting from 9 g of potassium 2,6-di-t-butyl-p-cresolate and from 1.2 g of cyclohexanone (phenate/substrate molar ratio = 3:1) in 40 cc of toluene and by operating according to the modalities of Example 2, 1.7 g of a mixture made up of cyclohexanone-2-carboxylic acid and cyclohexanone-2,6-dicarboxylic acid were obtained.

EXAMPLE 10

Starting from 9.5 g of potassium o-dodecyl-phenate, obtained in situ by salification with KOH of 8 g of o-dodecyl-phenol, and successive distillation of $H_2O$ azeotropically with toluene, as well as from 3.65 g of acetophenone (molar ratio = 1:1) in 40 cc of toluene, it was possible to obtain, by operating according to Example 1, 0.55 g of benzoylacetic acid.

Under the same conditions, potassium p-dodecyl-phenate did not result in any sensible reaction.

EXAMPLE 11

Starting from 7.35 g of potassium o-phenyl-phenate, obtained "in situ" by salifying 6 g of o-phenyl-phenol with KOH, and from 4.2 g of acetophenone (molar ratio = 1:1), it was possible to obtain, by operating as in Example 1, 0.5 g of benzoylacetic acid. Under the same conditions, potassium p-phenyl-phenate did not cause any sensible reaction.

EXAMPLE 12

Starting from 13.8 g of potassium o-t-butyl-phenate, obtained "in situ" by salifying 11 g of o-t-butyl-phenol with KOH, and from 8.8 g of acetophenone (molar ratio = 1:1) in 90 cc of toluene, it was possible to obtain, by operating according to Example 1, 1.5 g of benzoyl-acetic acid.

EXAMPLE 13

Starting from 7.5 g of potassium o-t-butyl-phenate obtained "in situ" by salifying 6 g of 2-t-butyl-phenol with KOH and from 4.7 g of phenyl-acetonitrile (molar ratio = 1:1) in 50 cc of toluene, and by operating as in Example 1, 1.47 g of phenyl-malonic acid mononitrile were obtained.

EXAMPLE 14

By operating according to Example 2, and starting from 4.4 g of potassium 2,6-di-t-butyl-phenate in 20 cc of toluene, as well as from 2.0 g of acetophenone (molar ratio = 1:1), 1.27 g of benzoylacetic acid were obtained.

EXAMPLE 15

By operating as in Example 2, and starting from 4.4 g of potassium 2,6-d-tert.-butyl-phenate -butyl-phenate as well as from 2.1 g of phenyl-acetonitrile (molar ratio = 1:1) in 20 cc of toluene, 1.4 g of phenyl-malonic acid mononitrile were obtained. 0.93 g of unaltered phenyl-acetonitrile were recovered.

EXAMPLE 16

By employing n-heptane instead of toluene and by operating under the same conditions as in Example 1, about 0.5 g of benzoylacetic acid were obtained.

EXAMPLE 17

Starting from 5.5 g of potassium 2,4,6-tri-t-butyl-phenate and from 2.2 g of acetophenone (molar ratio 1:1) in 20 cc of toluene it was possible to obtain, by operating according to Example 1, 0.74 g of benzoylacetic acid.

By operating at 50°C, as in Example 2, and using the same amounts of phenate and acetophenone, 1.28 g of benzoylacetic acid were obtained.

EXAMPLE 18

Starting from 8 g of potassium 2,4,6-tri-t-butyl-phenate and from 3.2 g of acetophenone (molar ratio = 1:1) in 35 cc of 1,2,4-trimethylbenzene and by operating as in Example 1, 1.05 g of benzoylacetic acid were obtained.

EXAMPLE 19

By operating as in Example 1 and starting from 13.8 g of potassium p-t-butyl-phenate, obtained "in situ" by salification with KOH of 11 g of p-t-butyl-phenol, as well as from 8.8 g of acetophenone (molar ratio = 1:1) in 120 cc of toluene, 0.75 g of benzoylacetic acid were obtained. By analogously operating in m-diisopropyl-benzene 0.86 g of benzoylacetic acid were obtained.

EXAMPLE 20

Starting from 8.8 g of potassium m-t-butylphenate, obtained "in situ" by salification of 7 g of 3-t-butyl phenol with KOH, and from 5.6 g of acetophenone (molar ratio = 1:1), it was possible to obtain, by operating according to the modalities of Example 1, 0.8 g of benzoylacetic acid.

EXAMPLE 21

Starting from 7.6 g of potassium m-t-butyl-phenate, obtained "in situ" by salification of 6 g of 3-t-butyl-phenol with KOH, and from 4.7 g of phenyl-acetonitrile in 50 cc of toluene, and following the modalities of Example 1, 1.22 of phenyl-malonic acid mononitrile were obtained.

EXAMPLE 22

By operating as in Example 2, starting from 6 g of potassium 2,6-di-methyl-phenate and from 4.5 g of acetophenone (molar ratio = 1:1) in 30 cc of toluene, 0.65 g of benzoylacetic acid were obtained.

EXAMPLE 23

By operating according to Example 2, starting from 9 g of potassium 2,6-dimethyl-4-dodecylphenate, obtained "in situ" by salification of 8 g of 2,6-dimethyl-4-dodecyl-phenol with KOH, and from 3.3 g of acetophenone (molar ratio = 1:1) in 50 cc of toluene, 0.95 g of benzoylacetic acid were obtained.

EXAMPLE 24

By operating according to Example 1, starting from 9.85 g of potassium 2-t-butyl-p-cresolate, obtained "in situ" by salification of 8 g of 2-t-butyl-p-cresol with KOH, and from 5.9 g of acetophenone (molar ratio = 1:1), 1.13 g of benzoylacetic acid were obtained.

EXAMPLE 25

By operating as in Example 1, starting from 6.75 g of potassium meta-cresolate and from 5.5 g of acetophenone, 0.55 g of benzoylacetic acid were obtained.

What we claim is:

1. A process for carboxylating organic substrates containing at least one activated hydrogen atom, which consists in reacting the substrate with $CO_2$ and an alkaline phenate selected from the group consisting of phenates substituted by
   a. an alkyl group containing from 3 to 30 carbon atoms bound to the phenolic nucleus in ortho or meta position or in para position through a tertiary or quaternary carbon atom;
   b. an alkyl group containing 1 to 20 carbon atoms bound to the phenolic nucleus in the ortho or meta positions through a primary or secondary carbon atom or by a phenyl group; and
   c. at least two alkyl groups containing 1 to 20 carbon atoms or phenyl groups in ortho and para positions;
in a hydrocarbon solvent selected from the group consisting of aliphatic, alicyclic, aromatic, and alkyl-substituted aromatic solvents.

2. The process according to claim 1, further characterized in that the solvent is selected from the group consisting of aliphatic, alicyclic, aromatic and alkyl-aromatic hydrocarbons having boiling points comprised between 80°C and 250°C.

3. The process according to claim 1, further characterized in that the solvent is at least one alkyl-aromatic hydrocarbon.

4. The process according to claim 1, further characterized in that the organic substrate is selected from the group consisting of ketones, esters, nitroparaffins and nitriles having the following general formulas:

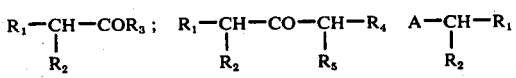

wherein:
$R_1$, $R_2$, $R_4$, $R_5$, which can be the same or different, represent H, an alkyl radical or an aryl radical;
$R_3$ is an alkyl or an aryl radical, or when $R_1$ is aryl, an o-alkyl or o-aryl group; and
$R_1$ and $R_4$ may also be bound to each other by alkyl chains; and
A is a $-NO_2$ group, a dinitro-aryl group, or when $R_1$ is aryl, a CN group.

5. The process according to claim 1, further characterized in that it is conducted at temperatures ranging from room temperature to 100°C.

6. The process according to claim 5, further characterized in that it is conducted at a temperature of about 50°C.

7. The process according to claim 1, further characterized in that for each mole of substrate from 1 to 4 moles of substituted phenate are employed.

8. The process according to claim 1, further characterized in that the substituted alkaline phenate is prepared in situ from the corresponding phenol and alkaline hydroxide under azeotropic removal, through the hydrocarbon solvent, of the reaction water.

* * * * *